(12) United States Patent
Jones et al.

(10) Patent No.: US 10,489,935 B2
(45) Date of Patent: Nov. 26, 2019

(54) SYSTEMS AND METHODS FOR DETERMINING CROWD TRAFFIC BY DETECTING DEBRIS IN FLOOR MATS

(71) Applicant: Walmart Apollo, LLC, Bentonville, AR (US)

(72) Inventors: Nicholaus Adam Jones, Fayetteville, AR (US); Robert James Taylor, Rogers, AR (US); Aaron James Vasgaard, Fayetteville, AR (US); Matthew Allen Jones, Bentonville, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 213 days.

(21) Appl. No.: 15/671,937

(22) Filed: Aug. 8, 2017

(65) Prior Publication Data

US 2018/0053323 A1 Feb. 22, 2018

Related U.S. Application Data

(60) Provisional application No. 62/375,523, filed on Aug. 16, 2016.

(51) Int. Cl.
*G06K 9/00* (2006.01)
*G06T 7/00* (2017.01)
*G01N 21/90* (2006.01)
*H04N 7/18* (2006.01)
(Continued)

(52) U.S. Cl.
CPC ............... *G06T 7/97* (2017.01); *G01N 21/90* (2013.01); *G06K 9/00771* (2013.01); *G07C 9/00* (2013.01);
(Continued)

(58) Field of Classification Search
CPC ........ G01N 21/59; G01N 21/90; G01N 21/94; G01N 2201/12; G06K 9/00;
(Continued)

(56) References Cited

U.S. PATENT DOCUMENTS 1,897,111 A * 2/1933 Corbett .................. G03B 15/00
396/155
2,262,435 A 11/1941 Waterman
(Continued)

FOREIGN PATENT DOCUMENTS

GB 2054369 2/1981
GB 2054369 A 2/1981

OTHER PUBLICATIONS

Environmental Science & Technology (ACS Publications), Measurements and Modeling of Deposited Particle Transport by Foot Traffic Indoors, http://pubs.acs.org/doi/abs/10.1021/es404886x, last viewed Apr. 19, 2016.

*Primary Examiner* — Tom Y Lu
(74) *Attorney, Agent, or Firm* — McCarter & English, LLP; David R. Burns

(57) ABSTRACT

Described in detail herein are methods and systems for determining crowd traffic in a facility by detecting debris on floor mats. The system can include floor mats disposed in a facility to collect debris from objects passing over the floor mats. A computing system can detect and estimate the amount of objects causing the debris on the floor mat. The computing system can estimate the amount of objects entering and exiting the facility based on the quantity of objects passing over the floor mats.

12 Claims, 7 Drawing Sheets

(51) Int. Cl.
*G07C 9/00* (2006.01)
*G01N 21/59* (2006.01)
*G01N 21/94* (2006.01)

(52) U.S. Cl.
CPC ............ *H04N 7/183* (2013.01); *G01N 21/59* (2013.01); *G01N 21/94* (2013.01); *G01N 2201/12* (2013.01); *G06T 2207/10016* (2013.01); *G06T 2207/10148* (2013.01); *G06T 2207/20012* (2013.01); *G06T 2207/20076* (2013.01); *G06T 2207/30242* (2013.01)

(58) Field of Classification Search
CPC ............ G06K 9/00771; G06Q 10/087; G06Q 30/0201; G06T 2207/10016; G06T 2207/10148; G06T 2207/20012; G06T 2207/20076; G06T 2207/30242; G06T 7/97; G07C 9/00; H04N 7/183
See application file for complete search history.

(56) References Cited

U.S. PATENT DOCUMENTS

| | | | |
|---|---|---|---|
| 4,630,110 A * | 12/1986 | Cotton | G07G 3/003 |
| | | | 200/86 R |
| 4,820,566 A | 4/1989 | Heine et al. | |
| 5,563,329 A | 10/1996 | Smith et al. | |
| 5,908,663 A | 6/1999 | Wang et al. | |
| 6,446,302 B1 | 9/2002 | Kasper et al. | |
| 8,812,344 B1 * | 8/2014 | Saurabh | G06K 9/00778 |
| | | | 705/7.29 |
| 2006/0171570 A1 | 8/2006 | Brendley et al. | |
| 2008/0212099 A1 * | 9/2008 | Chen | G06T 7/20 |
| | | | 356/408 |
| 2018/0075462 A1 * | 3/2018 | Jones | G06Q 30/0201 |
| 2018/0278996 A1 * | 9/2018 | Soundararajan | G06F 16/5838 |

* cited by examiner

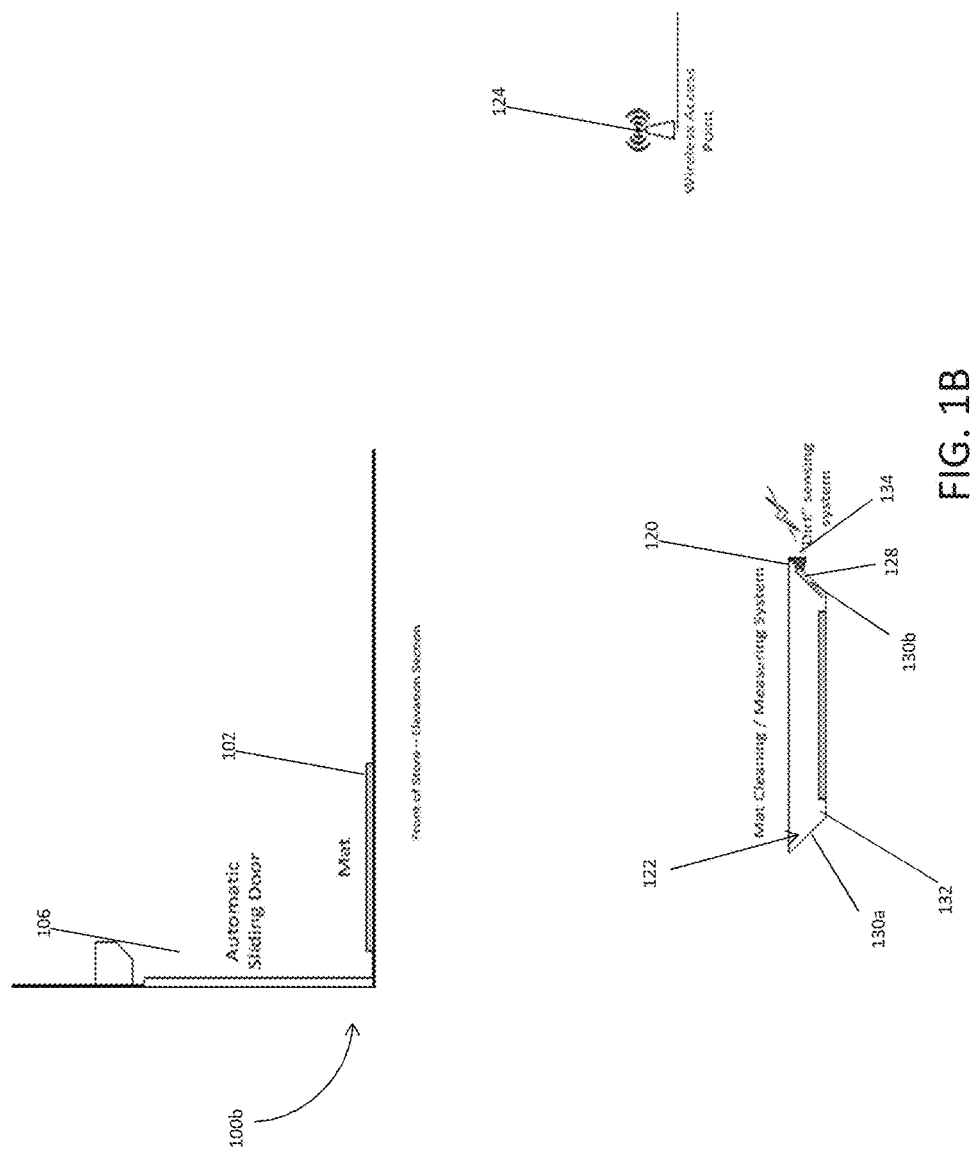

SYSTEMS AND METHODS FOR DETERMINING CROWD TRAFFIC BY DETECTING DEBRIS IN FLOOR MATS

CROSS-REFERENCE TO RELATED PATENT APPLICATIONS

This application claims priority to U.S. Provisional Application No. 62/375,523 filed on Aug. 16, 2016, the content of which is hereby incorporated by reference in its entirety

BACKGROUND

Monitoring crowd traffic in large facilities can be slow and error prone process.

BRIEF DESCRIPTION OF DRAWINGS

Illustrative embodiments are shown by way of example in the accompanying drawings and should not be considered as a limitation of the present disclosure:

FIG. 1B is a block diagram of another embodiment of a floor mat debris detection system according to the present disclosure;

DETAILED DESCRIPTION

Figure 1A:
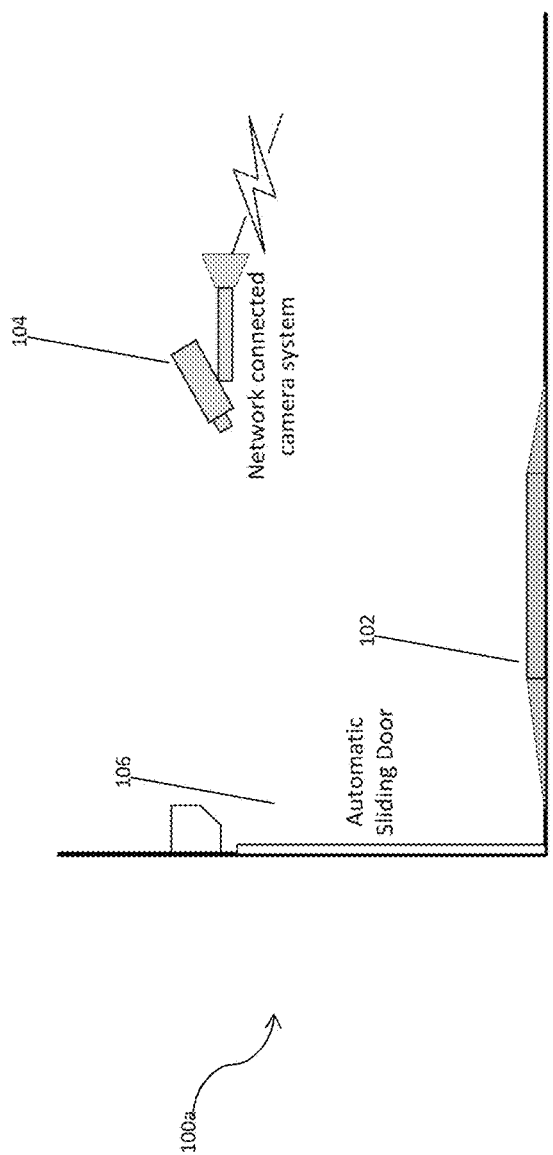
FIG. 1A is a block diagram of a floor mat debris detection system according to embodiments of the present disclosure.

Described in detail herein are methods and systems for estimating crowd traffic in a facility by detecting debris on floor mats. Embodiments of floor mat debris detection systems and methods can include floor mats disposed in a facility to collect debris from objects passing over the floor mats.

In accordance with embodiments of the present disclosure, image capturing device(s) can capture images of the debris on the floor mat and a computing system can detect and estimate the amount of objects causing the debris on the floor mat. The computing system can estimate the amount of objects entering and exiting the facility based on the quantity of objects passing over the floor mats.

Embodiments of the floor mat debris detection system includes a first floor mat disposed at a first location. The first floor mat is configured to receive debris from objects passing over the first floor mat. A first image capturing device is positioned to include the first floor mat in a field of view of the first image capturing device. The first image capturing device captures a first image of the first floor mat including the debris from the objects passing over the first floor mat. A computing system is operatively coupled to the first image capturing device. The computing system is programmed to analyze the first image to detect the amount debris on the first floor mat and to estimate a first quantity of objects that passed over the first floor mat based on the amount of the debris on the first floor mat.

A database stores a table associating the amount of debris in the first floor mat and the first quantity of objects expected to cause the amount of debris on the first floor mat. The computing system queries the database using the amount of debris on the first floor mat to determine the first quantity of object that passed over the first floor mat.

In some embodiments, a second floor mat configured to receive debris from objects passing over the second floor mat. The first image capturing device is positioned to include the first floor mat and the second floor mat in the field of view of the first image capturing device and is configured to capture, in the first image, the first floor mat and second floor mat. The computing system is programmed to analyze the first image and detect the first amount of debris on the first floor mat and a second amount of debris on the second floor mat and estimate the first quantity of objects passing over the first floor mat based on the first amount of debris and a second quantity of object passing over the second floor mat based on the second amount of debris.

In accordance with embodiments of the present disclosure, a container including a light source and sensor can detect debris on the floor mats. For example, the floor mats with debris can be placed inside the container for cleaning purposes. The container can be filled with a liquid and the sensor can illuminate the liquid before and after the floor mats are placed within the container and calculate the difference in the opaqueness in the liquid before and after the floor mats being placed in the container. The computing system can estimate the amount of objects causing the debris on the floor mats based on the difference in the opaqueness in the liquid and estimate the number of objects entering and exiting the facility.

Embodiments of the floor debris detection system can include a first floor mat disposed at a first location. The first floor mat configured to receive debris from objects passing over the first floor mat. The system includes a container including two sidewalls and a bottom wall. The two sidewalls and the bottom wall create a volume configured to receive the first floor mat with the debris and a liquid. The debris from the first floor mat is transferred to the liquid in the container. The container can include a light source configured to illuminate the volume of the container and a light sensor configured to sense a first opaqueness of the liquid in the container before first floor mat is received by the container and to sense a second opaqueness of the liquid subsequent to the first floor mat being received by the container. The floors mats can be placed in the container after a time period elapses and/or at periodic time increments.

Embodiments of the floor mat debris detection system can further include a computing system operatively coupled to the light sensor. The computing system can be programmed to determine estimate a first quantity of objects that passed over the first floor mat based on the first opaqueness and the second opaqueness of the liquid. The objects can be one or more of a user, a cart or a physical object. The computing system can retrieve an estimate of objects passing over the floor mats by querying a database which stores a table associating a difference between the first opaqueness and the second opaqueness of the liquid with an expected estimated quantity of objects required to cause the difference.

In some embodiments, the system includes a second floor mat disposed at a second location of the facility. The computing system is programmed to determine a second quantity of objects passing over the second floor mat.

FIG. 1A depicts a floor mat debris detection system 100A according to the present disclosure. The floor mat debris detection system 100A includes a floor mat 102 disposed in location in a facility. For example, the floor mat 102 can be disposed at the entrance/exit of the facility, e.g., proximate to front of the door 106. The floor mat 102 can receive and collect debris from objects traveling over the floor mat 102. For example, as the object travel over the floor mat 102, debris on the objects can be transferred to the floor mat 102 and can be retained by the material of the floor mat 102. The debris can include materials/matter from various indoor and outdoor environments, such as dirt, soil, rocks, leaves, dust, paint, and/or other fragments or particles. In some embodiments, the debris transferred to the floor mat 102 can cause the floor mat 102 to change color. A degree to which the floor mat 102 changes in color can be indicative of a quantity of objects that traveled over the floor mat 102. In some embodiments, the floor mat 102 can receive the debris in a localized area of the floor mat 102. Alternatively, the floor mat 102 can receive the debris throughout the surface of the floor mat.

The floor mat debris detection system 100A can also include an image capturing device 104 positioned to include the floor mat 102 in a field of view of the image capturing device 104. For example, the image capturing device 104 can be positioned above the floor mat 102. The image capturing device 104 can be configured to periodically or continuously capture images of the floor mat 102. The image capturing device 104 can be a camera configured to take still images or moving images.

In some embodiments, the system 100A can detect debris on the floor mat 102 via the images captured by the image capturing device 104. The image capturing device 104 can capture multiple images of the debris on the floor mat 102 in multiple zoom levels and/or using one or more lens filters. The image capturing device 104 can detect the debris in the floor mat 102 based on a change of pixels in the field of view. In the case of debris in multiple localized areas of the surface of the floor mat 102, the image capturing device 104 can capture a single or multiple images of each of the localized areas of the surface in multiple zoom levels. Additionally, or in the alternative, the image capturing device 104 can capture images of the floor mat 102 after a predetermined amount of time and/or at period time increments. The image capturing device 104 can transmit the captured images to a computing system via a network or communication channel as described herein. The computing system can be configured to estimate the quantity of objects that traveled over the floor mat 102, as will be discussed herein.

FIG. 1B depicts an embodiment of the floor mat debris detection system 100B in accordance with the present disclosure. The floor mat debris detection system 100B includes a floor mat 102 disposed near the entry/exit point 106 and a floor mat cleaning container 120. The floor mat 102 can receive and collect debris from objects passing over the floor mat 102. The floor mat debris detection system 100B can estimate the traffic traveling over on the floor mat 102 based on the debris.

The floor mat cleaning container 120 have side walls 130a-b and a bottom wall 132 defining an interior volume 122. The interior volume 122 can be filled with liquid. The liquid can be water and/or a mixture of cleaning fluids. The floor mat 102 can be placed inside the floor mat cleaning container 120 so that the floor mat 102 is fully submerged in the liquid. The debris from the floor mat can dissolve or mix into the liquid. The floor mat cleaning container 120 can have a light source 128 and a sensor 134 affixed to one of the side walls of the floor mat cleaning container 120. The light source 128 can extend along the side wall 130b of the floor mat cleaning container 120. The light source 128 can produce ambient light to illuminate the liquid within the floor mat cleaning container 120. The sensor 134 can detect an amount of opaqueness of the liquid and transmit the amount of opaqueness to the computing system via a network 124 and the computing system can estimate the traffic travelling over the floor mat 102 based on the detected opaqueness from the sensor 134, as described herein.

The sensor 134 can be can be refractometers, turbidity sensors, impedance sensors, or any other suitable type of sensors. In one embodiment the sensor 134 can determine the quality of liquid in the floor mat cleaning container. The quality of the liquid can be a turbidity of the liquid, an index of refraction of the liquid and/or an electrical impedance of the liquid. In another embodiment, the sensor 134 can determine dynamic light scattering to calculate the dynamic viscosity and average particle size in the liquid. The sensor 134 can estimate sensor 134 can transmit the quality of the liquid and/or dynamic viscosity and average particle size in the liquid to the computing system so that the computing system can estimate the traffic travelling over the floor mat 102 based on the determined quality and/or dynamic viscosity and average particle size in the liquid, as described herein.

Figure 1C:
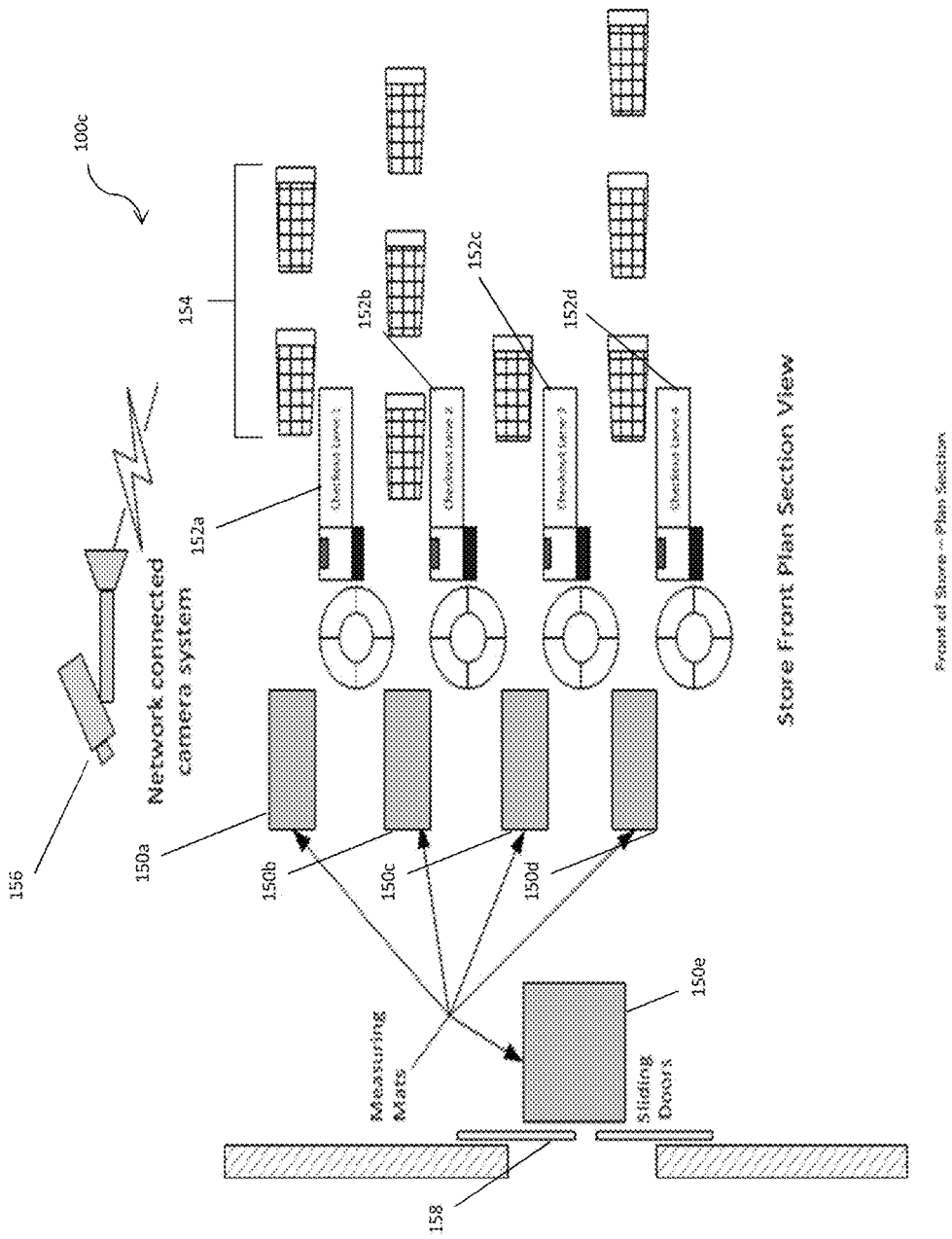
FIG. 1C is a block diagram of another floor mat debris detection system according to embodiments of the present disclosure.

FIG. 1C is a block diagram of an exemplary embodiment of the floor mat debris detection system 100C according to the present disclosure. As a non-limiting example, in the floor mat debris detection system 100C, the facility can be a retail store and the object which cause the debris on the floor mats can be people (including customers and employees) (not shown), shopping carts 154, and/or other objects. The retail store can have merchandise and multiple Point Of Sale (POS) terminals 152a-d disposed throughout the retail store. Each of POS terminals 152a-d can have a queue of shopping carts 154 at first end of the POS terminal and a floor mat 150a-d disposed at the second end of the POS station. For example, the POS terminal 152a can have a queue of shopping carts 154 at the first end and a floor mat 150a disposed at the second end of the POS terminal 152a. A floor mat 150e can be disposed at the front of the retail store in front of the door 158. An image capturing device 156 can be positioned above the floor mats 150a-e so that the floor mats are in the field of view of the image capturing device 156.

In exemplary embodiments, customers can enter the retail store from the front door 158. As the customers enter the retail store the customers can walk on the floor mat 150e. The floor mat can collect debris from the customers as the customers walk by (e.g., debris can be transferred from the customers' shoes to the floor mat 150e). As described with respect to FIG. 1, the image capturing device 156 can capture an image of the floor mat 150e of the floor mat with the debris. The image capturing device 156 can transmit the images to a computing system to determine the quantity of customers or shopping carts passing over the floor mat, via a network.

After entering the store, customers can shop for merchandise and place the merchandise in shopping carts 154 as they shop. The customers can form queues with the shopping carts 154 at the different POS terminals 152a-d to complete the payment and checkout process with their merchandise.

After the checkout process the customers can pass over the floor mat 150*a-d*. For example, a customer in the queue for POS terminal 152*a* can checkout and pass over the floor mat 150*a* with their shopping cart 154. In response to passing over the floor mat 150*a*, the floor mat 150*a* can collect debris from the customer's feet and the shopping cart's wheels. The image capturing device 156 can capture images of the floor mat 150*a* with the debris collected from the customer's feet and shopping cart's wheels. The image capturing device 156 can transmit the images of the floor mat 150*a* to detect the quantity of customers and shopping carts passing over the floor mat 150*a*. In other embodiments, the customer may checkout at POS terminal 152*a* and walk over floor mat 150*b-d*.

After completing the checkout process, the customer can exit the retail store using the door 158. As the customer exits the store, the customer can walk over the floor mat 150*e* with the shopping cart 154. The floor mat 150*e* can collect debris from the customer's feet and the shopping cart 154. The image capturing device 156 can capture an image of the floor mat 150*e* and transmit the images to the computing system to determine quantity of customers and shopping carts passing over the floor mat 150*e*. In some embodiments, the customer can exit without a shopping cart.

In some embodiments, a customer can pass over the floor mat 150*c* with a shopping cart 154 at the same time a customer passes over floor mat 150*a* with shopping cart 154. The image capturing device 156 can capture images of both floor mats 150*a* and 150*c* including the debris from the customer passing over floor mat 150*a* with shopping cart 154 and the debris caused by the customer passing over floor mat 150*c* with shopping cart 154. In some embodiments, one image can include both floor mat 150*a* and 150*c*. Alternatively, a single image of each floor mat (150*a* and 150*c*) is taken.

In some embodiments, multiple image capturing devices can be disposed around the retail store. One image capturing device can capture images of one or more floor mat disposed throughout the retail store.

In some embodiments, the floor mats can be disposed in various sections of the store. For example, a first floor mat may be disposed in the produce section, a second floor mat can be disposed in the electronics section and a third floor mat can be disposed in the clothing section.

In some embodiments, the floor mat debris detection system as shown in FIG. 1C can be implemented using embodiments of the floor mat debris detection system 100B with floor mat cleaning container 120 as described in FIG. 1B.

Figure 2:
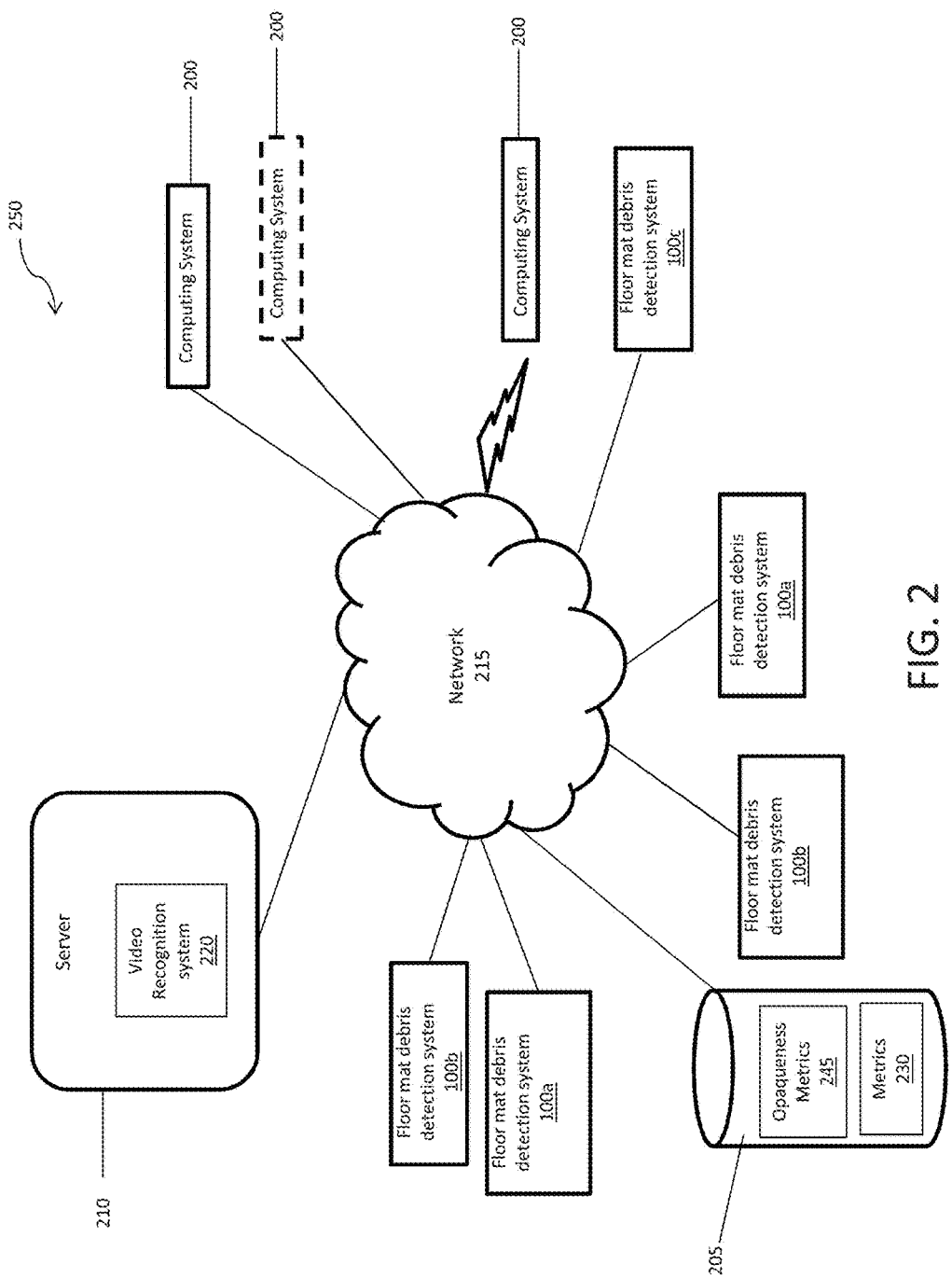
FIG. 2 illustrates a block diagram of a traffic detection system in accordance with embodiments of the present disclosure.

FIG. 2 is a block diagram illustrating a traffic detection system 250 according to exemplary embodiments. The traffic detection system 250 can include one or more databases 205, one or more servers 210, one or more computing systems 200 and instances of embodiments of a floor mat debris detection systems 100A, 100B, and/or 100C. The computing system 200 is in communication with the databases 205, the one or more servers 210, and the floor mat debris detection systems 100A, 100B, and/or 100C, via a communications network 215.

In an example embodiment, one or more portions of the communications network 215 can be an ad hoc network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a WiFi network, a WiMax network, any other type of network, or a combination of two or more such networks.

The server 210 includes one or more computers or processors configured to communicate with the computing system 200 and the databases 205, via the network 215. The server 210 hosts one or more applications configured to interact with one or more components computing system 200 and/or facilitates access to the content of the databases 205. The server 210 can also host the video recognition system 220 discussed herein. The databases 205 may store information/data, as described herein. For example, the databases 205 can include a opaqueness metrics database 245, and the metrics database 230. The databases 205 and server 210 can be located at one or more geographically distributed locations from each other or from the computing system 200. Alternatively, the databases 205 can be included within server 210.

In exemplary embodiments, the computing system 200 can receive multiple images from different instances of the floor mat debris detection system 100A. For example, the computing system 200 can receive an image from the floor mat debris detection system 100A of a debris on a floor mat disposed in a facility. The computing system 200 can execute the video recognition system 220 upon receiving the image. The video recognition system 220 can detect the debris in the image and analyze the debris using video analytics and/or machine vision. The types of machine vision can be but are not limited to: Stitching/Registration, Filtering, Thresholding, Pixel counting, Segmentation, Inpainting, Edge detection, Color Analysis, Blob discovery & manipulation, Neural net processing, Pattern recognition, and Gauging/Metrology. The video recognition system 220 can determine an amount of debris on the floor mat based on quantity of scattered fragments and a color change of the floor mat. The video recognition system 220 can determine change in color based on a plurality of pixels in the area of the debris. For example, the video recognition system 220 can detect various scattered fragments of dust, leaves, soil and other materials brought in from inside and outside the facility.

The video recognition system 220 can transmit the determined amount of debris to the computing system 200. The computing system 200 can query the metrics database 230 to retrieve a quantity of objects which correlate with the amount of debris on the floor mat. In response to retrieving a quantity of objects that correlate with the amount of debris on the floor mat the computing system 200 can estimate the amount of objects which caused the debris on the floor mat. Furthermore, if the floor mat is disposed at the entry and exit point of the facility the computing system can estimate the quantity of objects entering and exiting the facility. In some embodiments, the objects can be people, carts, wheelchairs, walkers, bikes, skateboards, or other transportation devices used within a facility.

In some embodiments, multiple floor mats can be disposed in various sections of the facility with at least one image capturing device positioned above the floor mats so that the floor mats are in the field of view of the image capturing device. The computing system 200 can receive an image of a floor mat disposed in an entry point of a particular section of the facility and an image of a floor mat at an exit point of a particular section of the facility. The floor mats can include a debris collected from objects passing over the floor mats. In response to receiving, images from the image capturing devices of the floor mats with debris, the computing system 200 can execute the video recognition system 220 and the video recognition system 220 can detect the debris and the quantity of debris upon entry and exit of the particular section. The video recognition system 220 can transmit the quantity of debris to the computing system 200. The computing system 200 can query the metrics database 230 to estimate the amount of objects causing the debris upon the entry point and exit point of the section. In some embodiments, the computing system 200 can determine the amount of time objects are spending in particular sections of the facility based on the entry time and exit time.

In some embodiments, the computing system 200 can receive an image with multiple floor mats. The video recognition system 220 can distinguish between the floor mats and between depressions in the floor mats in the image. For example, one image capturing device can capture an image of two floor mat disposed in respective sections. The video recognition system 220 can detect two different floor mats. For example, the video recognition system 220 can detect a space between the two floor mats to differentiate the floor mats. In another example, the floor mats can be different colors. The floor mats can collect different amount of debris. The video recognition system 220 can determine the different amount of debris based on a change in pixels between the images.

As a non-limiting example, the computing system 200 can receive an image of a floor mat disposed at the front of the retail store, near the entry and/or exit door. The image can have a debris on the floor mat caused by either a customer's shoe's or a shopping cart being used by the customer passing over the floor mat. The video recognition system 220 can detect the debris and determine an amount of debris on the floor mat. The video recognition system can transmit the amount of debris to the computing system 200. The computing system 200 can query the metrics database 230 to retrieve a quantity of objects that correlate with the amount of debris to estimate the amount of objects that passed over the floor mat. If the floor mat is placed at the entry or exit point of the retail store the computing system 200 can determine the amount of customers or shopping carts entering or exiting the retail store. The computing system 200 can calculate the difference of the amount customers or shopping carts entering the store as compared to the customers or shopping carts exiting the retail store cart. The computing system 200 can estimate the amount of customers exiting with products disposed at the facility based on the difference. In some embodiments, the computing system 200 can also determine the amount of time customers are spending within the retail store and how many customers are entering without shopping carts and exiting with shopping carts including products within the shopping carts.

In some embodiments, multiple floor mats can be disposed in various sections of the retail store. The computing system 200 can receive an image of a floor mat disposed in an entry point of a particular section of the retail store and an image of a floor mat at an exit point of a particular section of the retail store. The floor mats can include a debris collected from objects passing over the floor mats. In response to receiving, images from the image capturing devices of the floor mats with debris, the computing system 200 can execute the video recognition system 220 and the video recognition system 220 can detect the debris and the quantity of debris upon entry and exit of the particular section. The video recognition system 220 can transmit the quantity of debris to the computing system 200. The computing system 200 can query the metrics database 230 to estimate the amount of customers or shopping carts causing the debris upon the entry point and exit point of the section. The computing system 200 can estimate a number of customers or shopping carts entering and exiting the particular section of the store based on the quantity of customers or shopping carts causing the debris. In some embodiments, the computing system 200 can determine the amount of time objects are spending in particular sections of the facility based on the entry time and exit time.

In an alternative embodiment, the traffic detection system 250 can implement the floor mat debris detection system 100B. As mentioned above, the floor mat debris detection system with a container 100B can include a floor mat disposed at the entry or exit point of a facility with debris collected from objects passing over the floor mat. The floor mat debris detection system with a container 100B can calculate a difference in opaqueness in the liquid within a container before and after placing the floor mat in the container. The container can be used for cleaning purposes. The computing system 200 can receive an amount of the difference of opaqueness of the liquid. The computing system 200 can use the amount of difference in opaqueness of the liquid to query the opaqueness metrics database 245 to retrieve an amount of objects correlating with the difference in opaqueness of the liquid. The computing system 200 can estimate a number of objects passing over the floor mat based on the amount of objects which correlate with the difference in opaqueness of the liquid retrieved from the opaqueness database 245. The computing system 200 can determine the quantity of objects entering and exiting the facility. Once removed from the container the floor mat may not have any of the debris and can be disposed in the entry or exit point of the facility.

In an alternative embodiment, the traffic detection system 250 can implement the floor mat debris detection system 100C. As mentioned above, multiple floor mats can be disposed in various sections of the facility with each floor mat can get placed in a different containers filled with liquid for cleaning purposes. The floor mats can include a debris collected from objects passing over the floor mats and once placed in the container the debris can be removed from the floor mat and dissolved in the liquid. The computing system 200 can receive can receive an amount of the difference of opaqueness of the liquid for a floor mat disposed in an entry point of a particular section of the facility and an amount of the difference of opaqueness of the liquid for a floor mat a floor mat at an exit point of a particular section of the facility. In response to receiving amounts of the difference of opaqueness of the liquid, the computing system 200 can query the opaqueness metrics database 245 to estimate the amount of objects causing the debris upon the entry point and exit point of the section. In some embodiments, the computing system 200 can determine the amount of time objects are spending in particular sections of the facility based on the entry time and exit time.

Figure 3:
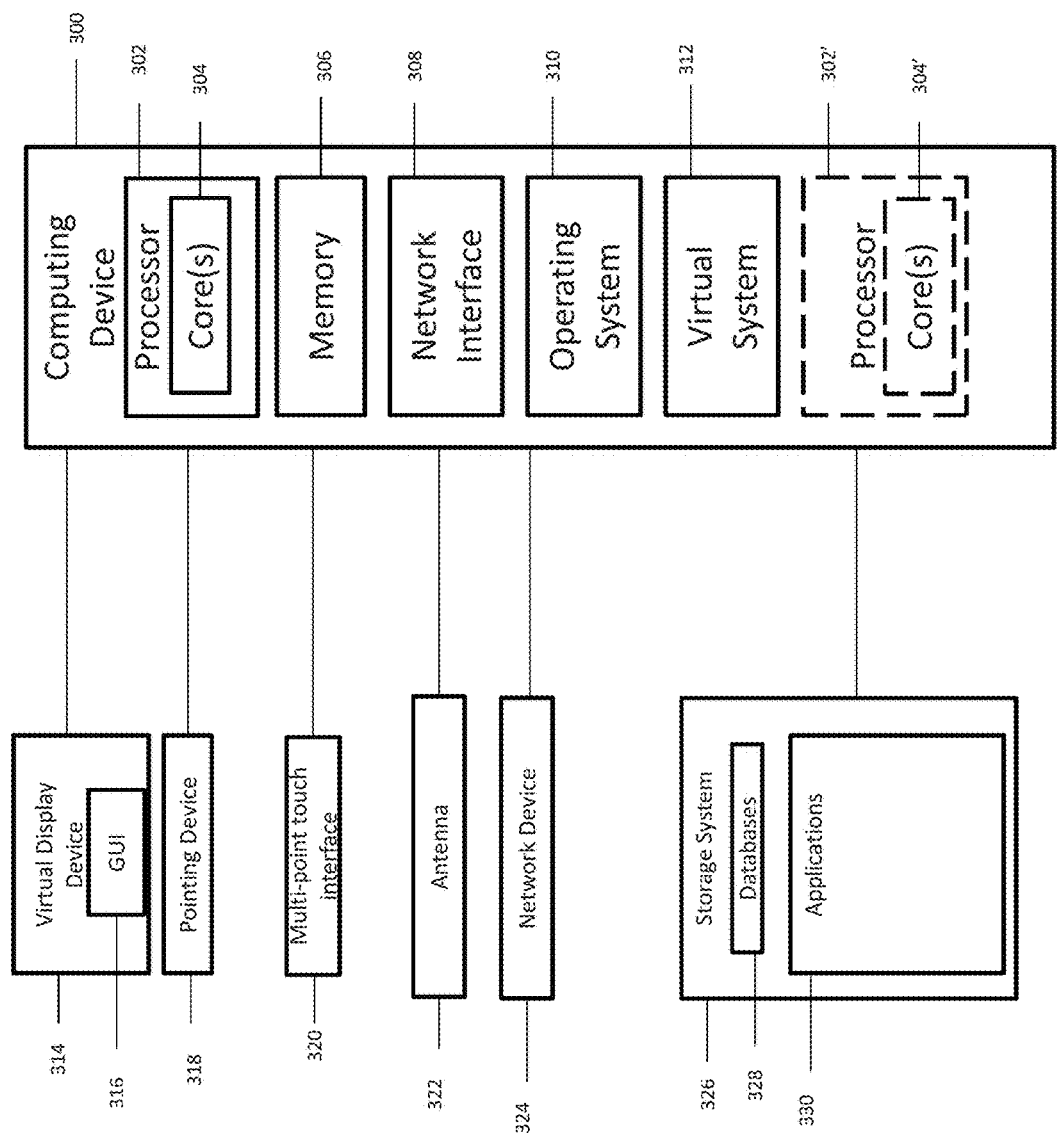
FIG. 3 illustrates an exemplary computing device in accordance with exemplary embodiments of the present disclosure.

FIG. 3 is a block diagram of an example computing device for implementing exemplary embodiments of the present disclosure. Embodiments of the computing device 300 can implement embodiments of portions of the floor mat debris detection systems 100A-C and/or the computing system 200 within the traffic detection system 250. The computing device 300 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives, one or more solid state disks), and the like. For example, memory 306 included in the computing device 300 may store computer-readable and computer-executable instructions or software (e.g., applications 330) for implementing exemplary operations of the computing device 300. The computing device 300 also includes configurable and/or programmable processor 302 and associated core(s) 304, and optionally, one or more additional configurable and/or programmable processor(s) 302' and associated core(s) 304' (for example, in the case of computer systems having multiple processors/cores), for executing computer-readable and computer-executable instructions or software stored in the memory 306 and other programs for implementing exemplary embodiments of the present disclosure. Processor 302 and processor(s) 302' may each be a single core processor or multiple core (304 and 304') processor. Either or both of processor 302 and processor(s) 302' may be configured to execute one or more of the instructions described in connection with computing device 300.

Virtualization may be employed in the computing device 300 so that infrastructure and resources in the computing device 300 may be shared dynamically. A virtual machine 312 may be provided to handle a process running on multiple processors so that the process appears to be using only one computing resource rather than multiple computing resources. Multiple virtual machines may also be used with one processor.

Memory 306 may include a computer system memory or random access memory, such as DRAM, SRAM, EDO RAM, and the like. Memory 306 may include other types of memory as well, or combinations thereof.

A user may interact with the computing device 300 through a visual display device 314, such as a computer monitor, which may display one or more graphical user interfaces 316, multi touch interface 320 and a pointing device 318.

The computing device 300 may also include one or more storage devices 326, such as a hard-drive, CD-ROM, or other computer readable media, for storing data and computer-readable instructions and/or software that implement exemplary embodiments of the present disclosure (e.g., applications). For example, exemplary storage device 326 can include one or more databases 328 for storing information regarding crowd traffic and debris collected by a floor mat. The databases 328 may be updated manually or automatically at any suitable time to add, delete, and/or update one or more data items in the databases. The databases 328 can include information such as opaqueness metrics database 245 and metrics database 230.

The computing device 300 can include a network interface 308 configured to interface via one or more network devices 324 with one or more networks, for example, Local Area Network (LAN), Wide Area Network (WAN) or the Internet through a variety of connections including, but not limited to, standard telephone lines, LAN or WAN links (for example, 802.11, T1, T3, 56kb, X.25), broadband connections (for example, ISDN, Frame Relay, ATM), wireless connections, controller area network (CAN), or some combination of any or all of the above. In exemplary embodiments, the computing system can include one or more antennas 322 to facilitate wireless communication (e.g., via the network interface) between the computing device 300 and a network and/or between the computing device 300 and other computing devices. The network interface 308 may include a built-in network adapter, network interface card, PCMCIA network card, card bus network adapter, wireless network adapter, USB network adapter, modem or any other device suitable for interfacing the computing device 300 to any type of network capable of communication and performing the operations described herein.

The computing device 300 may run any operating system 310, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device 300 and performing the operations described herein. In exemplary embodiments, the operating system 310 may be run in native mode or emulated mode. In an exemplary embodiment, the operating system 310 may be run on one or more cloud machine instances.

Figure 4:
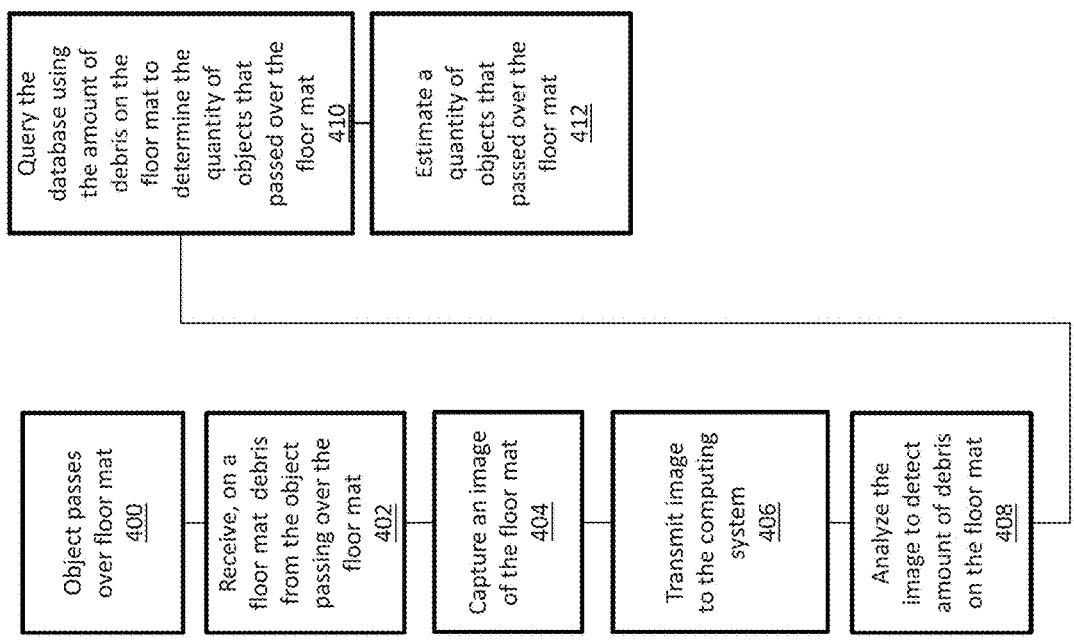
FIG. 4 is a flowchart illustrating a process of the traffic detection system including an embodiment of the floor mat debris detection system according to exemplary embodiments of the present disclosure.

FIG. 4 is a flowchart illustrating a process implemented by an embodiment of the traffic detection system including an embodiment of the floor mat debris detection system (e.g. floor mat debris detection system 100 as shown in FIGS. 1A and 1C). In operation 400, objects pass over a floor mat (e.g. floor mat 102 and 150*a*-*e* shown in FIGS. 1A and 1C) disposed in a facility. For example the floor mat can be disposed near the entry/exit point (e.g. door 106 and 158 shown in FIGS. 1A and 1C). The object can be a person, cart, walking aid or any mode of transportation used within a facility. An image capturing device (e.g., image capturing device 104 and 156 shown in FIGS. 1A and 1C) can be positioned over the floor mat so that the floor mat is in the field of view of the image capturing device.

In operation 402, the floor mat can receive debris from the objects passing over the floor mat. Debris can be but are not limited to: dirt, soil, grass, rocks, dust, mud, branches, leaves, water, and other types of items found in an outdoor or indoor environment. For example, a person can walk into the facility and the shoes of the person can leave debris of dirt on the floor mat. In another example, a cart can be pushed over the floor mat and the wheels of the cart can leave dust from the wheels of the cart on the cart.

In operation 404, the image capturing device can capture an image of the floor mat. The image capturing device can capture images of the floor mat after predetermined amount of time. In other embodiments, the image capturing device can capture an image of the floor mat in response to detecting objects passing over the floor mat.

In operation 406, the image capturing device can transmit the image of the floor mat to the computing system (e.g., computing system 200 shown in FIG. 2). In operation 408, the computing system can execute the video recognition system (e.g., video recognition system 220 shown in FIG. 2) to analyze the image to determine an amount of debris on the floor mat. The video recognition system can use video analytics and/or machine vision to detect the amount of debris on the floor mat. For example, the video recognition system can detect the difference in color in the portion of the floor mat the debris have been received as compared to the remaining portion of the floor mat.

In operation 410, the computing system can query the metrics database using the determined amount of debris on the floor mat to retrieve a quantity of objects correlated to the amount of debris. The metrics database can store the amounts of debris correlated with the quantity of objects that may cause the amounts of debris.

In operation 412, the computing system can estimate the quantity of objects which caused the amount of debris on the floor mat. The quantity objects can correlate to a quantity of people and physical objects entering and exiting the facility.

Figure 5:
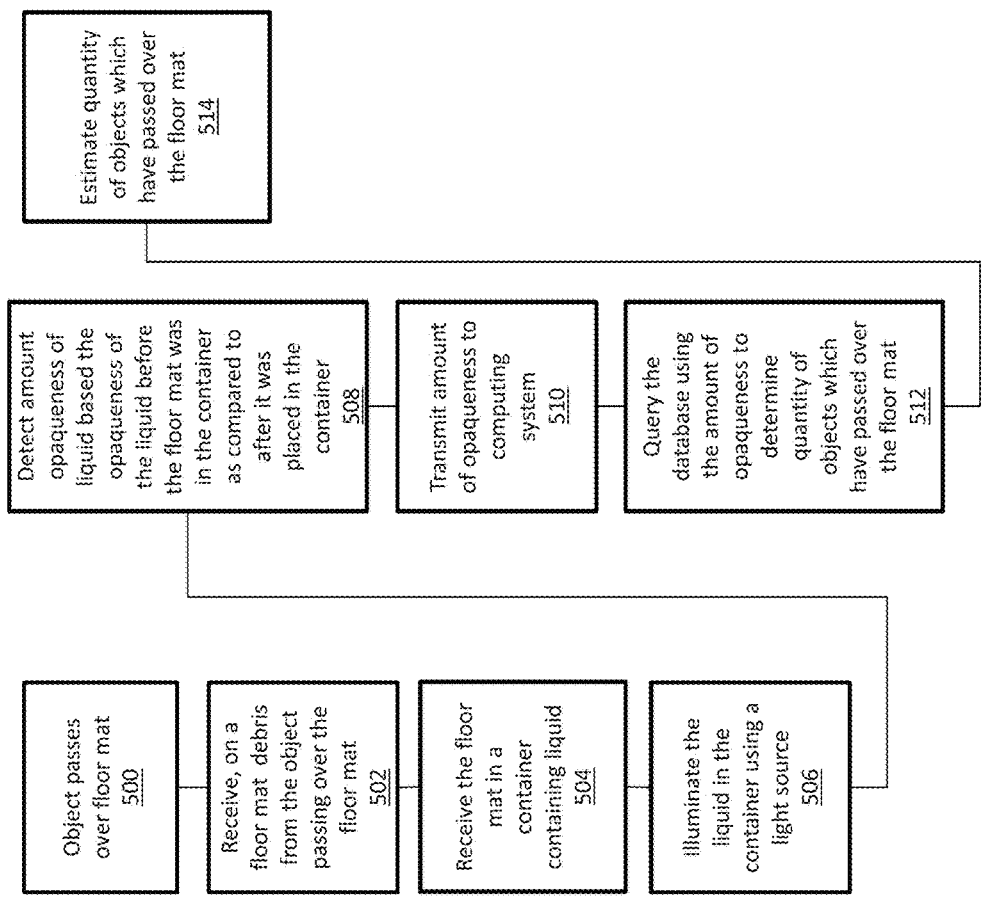
FIG. 5 is a flowchart illustrating a process of the traffic detection system including an embodiment of the floor mat debris detection system according to the present disclosure.

FIG. 5 is a flowchart illustrating a process of a traffic detection system including an embodiment of the floor mat debris detection system as shown in FIG. 1B 100B. In operation 500, objects passes over a floor mat (e.g. floor mat 102 shown in FIG. 1B) disposed in a facility. For example, the floor mat 102 can be disposed near the entry/exit point (e.g. door 106 shown in FIG. 1B). In operation 502, the floor mat can receive debris from the objects passing over the floor mat.

In operation 504, the floor mat can be placed into a container containing a liquid within an interior volume. Prior to placing the floor mat in the container the liquid can be transparent. In some embodiments, the liquid can be tap water. In other embodiments, the liquid can be tap water combined with cleaning fluids. Subsequent to putting the floor mat in the container the liquid's opaqueness can change.

In operation 506, an a light can be illuminate can the liquid in the container. The light can be illuminate the liquid prior to the floor mat being placed and a light sensor can detect an amount of opaqueness in the liquid.

In operation 508, the light sensor can detect the amount of opaqueness of the liquid after the floor mat has been placed inside the container. The light sensor can compare the opaqueness of the liquid before placing the floor mat in the liquid and the opaqueness of the liquid after placing the floor mat in the liquid and calculate the difference.

In operation 510, the light sensor can transmit the difference in opaqueness in the liquid to the computing system. In operation 512, the computing system can query the metrics database to retrieve a quantity of objects correlated with the difference in the opaqueness. In operation 514, based on the retrieved quantity of objects, the computing system can estimate a quantity of objects that have passed over the floor mat at the time the image was taken.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

We claim:

1. A system for detecting crowd traffic, the system comprising:
   a first floor mat disposed at a first location, the first floor mat configured to receive debris from objects passing over the first floor mat;
   a first image capturing device positioned to include the first floor mat in a field of view of the first image capturing device, the first image capturing device being configured to capture a first image of the first floor mat including the debris from the objects passing over the first floor mat; and
   a computing system operatively coupled to the first image capturing device, the computing system being programmed to analyze the first image to detect the amount debris on the first floor mat and to estimate a first quantity of objects that passed over the first floor mat based on the amount of the debris on the first floor mat.

2. The system in claim 1, further comprising a database storing a table associating the amount of debris in the first floor mat and the first quantity of objects expected to cause the amount of debris on the first floor mat.

3. The system in claim 2, wherein the computing system queries the database using the amount of debris on the first floor mat to determine the first quantity of object that passed over the first floor mat.

4. The system in claim 1, further comprising, a second floor mat configured to receive debris from objects passing over the second floor mat.

5. The system in claim 4, wherein the first image capturing device is positioned to include the first floor mat and the second floor mat in the field of view of the first image capturing device and is configured to capture, in the first image, the first floor mat and second floor mat.

6. The system in claim 5, wherein the computing system is programmed to analyze the first image and detect the first amount of debris on the first floor mat and a second amount of debris on the second floor mat and estimate the first quantity of objects passing over the first floor mat based on the first amount of debris and a second quantity of object passing over the second floor mat based on the second amount of debris.

7. A method for detecting crowd traffic, the method comprising:
   receiving, on a first floor mat at a first location, debris from objects passing over the first floor mat;
   capturing, via a first image capturing device positioned to include the first floor mat in a field of view of the first image capturing device, a first image of the first floor mat including the debris from the objects passing over the first floor mat;
   analyzing, via a computing system operatively coupled to the first image capturing device, the first image to detect amount of debris on the first floor mat and estimate a first quantity of objects that passed over the first floor mat based on the amount of the debris on the first floor mat.

8. The method in claim 7, further comprising, storing, via a database coupled to the computing system, a table associating the amount of debris in the first floor mat and the first quantity of objects expected to cause the amount of debris on the first floor mat.

9. The method in claim 8, further comprising, querying the database, via the computing system, using the amount of debris on the first floor mat to determine the first quantity of object that passed over the first floor mat.

10. The method in claim 7, further comprising, receiving on a second floor mat debris from objects passing over the second floor mat.

11. The method in claim 10, wherein the first image capturing device positioned to include the first floor mat and the second floor mat in the field of view of the first image capturing device, and capturing the first image includes capturing the first floor mat and second floor mat in the first image.

12. The method in claim 11, further comprising: analyzing, via the computing system, the first image to detect the first amount of debris on the first floor mat and a second amount of debris on the second floor mat and estimate a first quantity of objects passing over the first floor mat based on the first amount of debris and a second quantity of object passing over the second floor mat based on the second amount of debris.

* * * * *